United States Patent [19]

Jonischkeit

[11] Patent Number: 4,861,339
[45] Date of Patent: Aug. 29, 1989

[54] INJECTION SPRAY GUN WITH ADJUSTABLE PRESSURE LIMITATION

[75] Inventor: Horst Jonischkeit, Tuttlingen, Fed. Rep. of Germany

[73] Assignee: Henke-Sass, Wolf GmbH, Tuttlingen, Fed. Rep. of Germany

[21] Appl. No.: 55,625

[22] PCT Filed: Sep. 24, 1986

[86] PCT No.: PCT/DE86/00392
§ 371 Date: May 26, 1987
§ 102(e) Date: May 26, 1987

[87] PCT Pub. No.: WO87/01945
PCT Pub. Date: Apr. 9, 1987

[30] Foreign Application Priority Data

Sep. 25, 1985 [DE] Fed. Rep. of Germany ....... 3534215

[51] Int. Cl.⁴ .............................................. A61M 1/00
[52] U.S. Cl. .................... 604/118; 604/187; 604/232
[58] Field of Search ............... 604/187, 218, 121, 118, 604/232, 234, 233

[56] References Cited

U.S. PATENT DOCUMENTS

| | | | |
|---|---|---|---|
| 3,905,365 | 9/1975 | Colombo | 604/233 |
| 4,014,331 | 3/1977 | Head | 604/187 |
| 4,632,669 | 12/1986 | Phipps, Sr. et al. | 604/118 |

FOREIGN PATENT DOCUMENTS

| | | | |
|---|---|---|---|
| 3325046 | 1/1985 | Fed. Rep. of Germany | 604/187 |
| 3408618 | 9/1985 | Fed. Rep. of Germany | 604/232 |
| 8006197 | 6/1982 | Netherlands | 604/232 |
| 2162426 | 2/1986 | United Kingdom | 604/187 |

Primary Examiner—C. Fred Rosenbaum
Assistant Examiner—Mark F. Colosimo
Attorney, Agent, or Firm—Spencer & Frank

[57] ABSTRACT

An injection spray gun with a holder comprising: a sheathing adapted to receive a cylindrical ampule; a handle fastened to the gun; an actuating lever pivotally attached to the handle; a plunger guided in the holder and connected with the actuating lever; a piston located in the cylindrical ampule wherein movement of the plunger causes forward thrust of the piston; and a pressure limiting device being provided for acting on at least one of the actuating lever and/or the plunger.

16 Claims, 1 Drawing Sheet

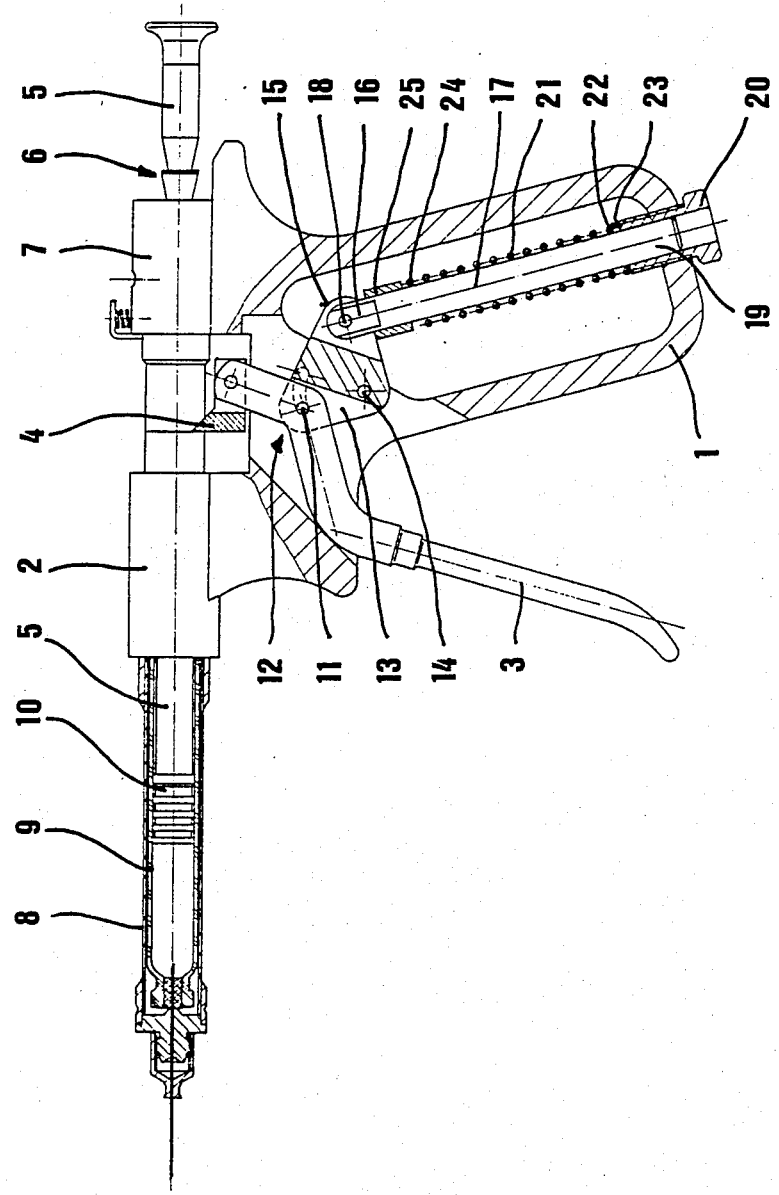

INJECTION SPRAY GUN WITH ADJUSTABLE PRESSURE LIMITATION

BACKGROUND OF THE INVENTION

1. Field of the Invention

The invention relates to an injection spray gun with a holder configured for the attachment of a sheathing provided to receive a cylindrical ampule, a handle connected therewith, an actuating lever attached pivotally thereto and a plunger, guided in the holder and connected with the actuating lever, causing the forward thrust of a piston located in the cylindrical ampule.

2. Discussion of the Prior Art

Such injection spray guns are used for various medical purposes, especially by dentists for intraligamental anesthesia. The advantage of such a spray gun is that it can produce a very high pressure for each individual spray process.

However the drawback with such injection spray guns is that the doctor using the instrument must control and limit the pressure which is produced purely by touch, in order to prevent the breaking open of the cylindrical ampule which is being used (containing the solution which is to be sprayed) and the washing of a tooth, to be treated, out of its paradontal tooth socket (alveolar cavity) or at least its being worked loose.

SUMMARY OF THE INVENTION

The object of the present invention is therefore to construct an injection spray gun in such a manner that the pressure exerted by the lever mechanism on the fluid to be sprayed can be limited and even adjusted and controlled.

This object is attained in that with an injection spray gun of this type, a pressure limiting device is provided on actuating lever and/or plunger.

According to the invention, this pressure limiting device consists essentially of a spring element and a two-arm shift lever.

It is advantageous that the actuating lever be fastened to the handle by the two-arm shift lever, and the two-arm shift lever be mounted pivotally on an axis arranged in the handle. The actuating lever with its pivot axis is fastened pivotally on the first arm of the shift lever and the spring element operatively engages the second arm of the shift lever.

With this arrangement, the shift lever acts as a block for the actuating lever, and this block can deflect the pressure originated by the actuating lever when it has attained a certain level and upon release of this pressure can return to its original position. The spring element forms the adjustable block force.

It is advantageous that the spring element be configured as a helical spring and arranged on a guide rod. This guide rod is mounted flexibly or by articulation with its first end on the second arm of the shift lever and its second end projects into an adjusting screw installed in the handle. One end of the spring element engages the rim of the adjusting screw.

This prescribed combination of spring element and guide rod allows precise adjustability of the block pressure caused by the spring element.

BRIEF DESCRIPTION OF THE DRAWING

The invention may be better understood by referring to the detailed description of the invention when taken in conjunction with the accompanying drawings in which:

The sole FIGURE shows a partially cut open side view of an injection spray gun according to the invention.

DETAILED DESCRIPTION OF THE PREFERRED EMBODIMENT

The injection spray gun shown in the drawing consists essentially of a handle 1, a holder 2 configured in one piece with the handle, and an actuating lever 3, mounted pivotally in the handle, which actuates a pawl 4 through a lever mechanism built into the handle and explained in more detail hereinafter, which engages sequentially in driving arms 6 formed on plunger 5 and causes the advance of plunger 5 following any actuation of actuating lever 3. Plunger 5 is guided in holder 2 and also in an additional guide member 7 on handle 1.

A sheathing 8 is introduced into holder 2, in which is also inserted a piston 10 closing the cylindrical ampule 9 containing the medication to be sprayed in from the outside. The sheathing-like end of plunger 5 comes into engagement on piston 10 and presses the piston into a cylindrical ampule 9 during the spraying process.

Actuating lever 3 is mounted pivotally with its pivot axis 11 not directly in handle 1, but on the first arm 12 of a two-arm shift lever 13, which in turn is fastened pivotally in handlle 1 around an axis 14. The top end 16 of a guide rod 17 is pivotally fastened about axis 18 to second arm 15 of the two-arm shift lever 13. The bottom end 19 of guide rod 17 projects into an adjusting screw 20 configured as a hollow body, which in turn is adjustable lengthwise in handle 1.

A helical spring element 21 is arranged on guide rod 17, with its bottom end 22 coming into contact with the rim 23 of adjusting screw 20 and with its top end 24 engaging on a sheathing 25 arranged on guide rod 17.

The operation of the lever mechanism is as follows:

The doctor making use of the injection gun for an injection moves actuating lever 3 against handle 1, and actuating lever 3 pivots around pivot axis 11 and moves pawl 4 together with plunger 5 against piston 10.

The pivot axis or pivot point 11 of actuating lever 3 on shift lever 13, stabilized by the force of spring element 21, forms the block, which nonetheless withdraws from actuating lever 3 with a force exceeding the force of spring element 21. The shift lever 13 is therefore pivoted around its mounting axis 14 in handle 1 and guide rod 17 is sunk partially into the hollow body of the adjusting screw 20, and as a result of this shift of bearing point 11, actuating lever 3 can be pressed down as far as the mechanical stop of guide rod 17 in adjusting screw 20, without increasing the injection pressure.

When actuating lever 3 is presssed down entirely and shift lever 13 is deflected, spring element 21 assumes the injection until pivot point 11 is pressed back into original position.

This pressure controlled lever mechanism guarantees on the one hand that bursting of the cylindrical ampule on account of on exceedingly high pressure is no longer possible, and on the other hand, that paradontal teeth cannot be loosened and/or removed from their tooth socket by the intraligamental injection.

What is claimed is:

1. An injection spray gun with a holder configured for attachment of a sheathing provided to receive a cylindrical ampule containing a piston comprising: a handle fastened to said holder; an actuating lever pivotally attached to said handle; a plunger guided in said holder and connected with said actuating lever so that when the sheathing is attached to said holder, movement of said plunger causes forward thrust of the piston; and a pressure limiting device connected for acting on at least one of said actuating lever and said plunger.

2. An injection spray gun as defined in claim 1, wherein said pressure limiting device comprises a spring element having a top and bottom end and a two-arm shift lever which has a first arm and a second arm.

3. An injection spray gun as defined in claim 2, wherein said actuating lever is fastened to said handle with interposition of said two-arm shift lever, and said two-arm shift lever is pivotally mounted on a transverse axis arranged in said handle, said actuating lever being pivotally fastened on said first arm of said shift lever; and said spring element engages said second arm of said shift lever.

4. An injection spray gun as defined in claim 3, wherein said spring element comprises a helical spring; and said gun further comprises a guide rod having a first and second end and an adjusting screw having a rim; said helical spring being arranged on said guide rod, and said guide rod being mounted flexibly with said first end on said second arm of said shift lever and with said second end of said guide rod projecting into said adjusting screw which is introduced into said handle and said bottom end of said spring element engages on said rim of said adjusting screw.

5. An injection spray gun with a holder comprising: a cylindrical ampule; a sheathing having said cylindrical ampule disposed therein; a handle fastened to said holder; an actuating lever pivotally attached to said handle; a plunger guided in said holder and connected with said actuating lever; a piston located in said cylindrical ampule wherein movement of said plunger causes forward thrust of said piston; and a pressure limiting device being provided for acting on at least one of said actuating lever and said plunger.

6. An injection spray gun as defined in claim 5, wherein said pressure limiting device comprises a spring element having a top and bottom end and a two-arm shift lever which has a first arm and a second arm.

7. An injection spray gun as defined in claim 6, wherein said actuating lever is fastened to said handle with interposition of said two-arm shift lever, and said two-arm shift lever is pivotally mounted on a transverse axis arranged in said handle, said actuating lever being pivotally fastened on said first arm of said shift lever; and said spring element engages said second arm of said shift lever.

8. An injection spray gun as defined in claim 7, wherein said spring element comprises a helical spring; and said gun further comprise a guide rod having a first and second end and an adjusting screw having a rim; said helical spring being arranged on said guide rod, and said guide rod being mounted flexibly with said first end on said second arm of said shift lever and with said second end of said guide rod projecting into said adjusting screw which is introduced into said handle and said bottom end of said spring element engages on said rim of said adjusting screw.

9. An injection spray gun with a holder configured for attachment of a sheathing provided to receive a cylindrical ampule containing a piston comprising: a handle fastened to said holder; an actuating lever pivotally attached to said handle and extending outside said handle and said holder; a plunger guided in said holder and connected with said actuating lever so that when the sheathing is attached to said holder, movement of said plunger causes forward thrust of the piston; and a pressure limiting device connected for acting on at least one of said actuating lever and said plunger.

10. An injection spray gun as defined in claim 9, wherein said pressure limiting device comprises a spring element having a top and bottom end and a two-arm shift lever which has a first arm and a second arm.

11. An injection spray gun as defined in claim 10, wherein said actuating lever is fastened to said handle with interposition of said two-arm shift lever, and said two-arm shift lever is pivotally mounted on a transverse axis arranged in said handle, said actuating lever being pivotally fastened on said first arm of said shift lever; and said spring element engages said second arm of said shift lever.

12. An injection spray gun as defined in claim 11, wherein said spring element comprises a helical spring; and said gun further comprises a guide rod having a first and second end and an adjusting screw having a rim; said helical spring being arranged on said guide rod, and said guide rod being mounted flexibly with said first end on said second arm of said shift lever and with said second end of said guide rod projecting into said adjusting screw which is introduced into said handle and said bottom end of said spring element engages on said rim of said adjusting screw.

13. An injection spray gun with a holder comprising: a cylindrical ampule; a sheathing having said cylindrical ampule disposed therein; a handle fastened to said holder; an actuating lever pivotally attached to said handle and extending outside said handle and said holder; a plunger guided in said holder and connected with said actuating lever; a piston located in said cylindrical ampule wherein movement of said plunger causes forward thrust of said piston; and a pressure limiting device being provided for acting on at least one of said actuating lever and said plunger.

14. An injection spray gun as defined in claim 13, wherein said pressure limiting device comprises a spring element having a top and bottom end and a two-arm shift lever which has a first arm and a second arm.

15. An injection spray gun as defined in claim 14, wherein said actuating lever is fastened to said handle with interposition of said two-arm shift lever, and said two-arm shift lever is pivotally mounted on a transverse axis arranged in said handle, said actuating lever being pivotally fastened on said first arm of said shift lever; and said spring element engages said second arm of said shift lever.

16. An injection spray gun as defined in claim 15, wherein said spring element comprises a helical spring; and said gun further comprises a guide rod having a first and second end and an adjusting screw having a rim; said helical spring being arranged on said guide rod, and said guide rod being mounted flexibly with said first end on said second arm of said shift lever and with said second end of said guide rod projecting into said adjusting screw which is introduced into said handle and said bottom end of said spring element engages on said rim of said adjusting screw.

* * * * *